US012672896B2

(12) United States Patent
Sweis et al.

(10) Patent No.: US 12,672,896 B2
(45) Date of Patent: Jul. 7, 2026

(54) SURGICAL DRAIN DEVICE AND METHOD OF USE

(71) Applicant: Standard of Care Corporation, Chicago, IL (US)

(72) Inventors: Iliana E. Sweis, Chicago, IL (US); Bryan C. Cressey, Chicago, IL (US)

(73) Assignee: Standard of Care Corporation, Deefield, IL (US)

( * ) Notice: Subject to any disclaimer, the term of this patent is extended or adjusted under 35 U.S.C. 154(b) by 0 days.

(21) Appl. No.: 18/047,529

(22) Filed: Oct. 18, 2022

(65) Prior Publication Data

US 2023/0111020 A1 Apr. 13, 2023

Related U.S. Application Data

(63) Continuation of application No. PCT/US2022/016410, filed on Feb. 15, 2022.

(60) Provisional application No. 63/150,022, filed on Feb. 16, 2021.

(51) Int. Cl.
| | |
|---|---|
| *A61B 17/34* | (2006.01) |
| *A61M 27/00* | (2006.01) |
| *A61B 17/00* | (2006.01) |
| *A61B 90/00* | (2016.01) |

(52) U.S. Cl.
CPC ...... *A61B 17/3417* (2013.01); *A61B 17/3415* (2013.01); *A61M 27/00* (2013.01); *A61B 2017/0042* (2013.01); *A61B 2017/00477* (2013.01); *A61B 2017/00738* (2013.01); *A61B 2017/3456* (2013.01); *A61B 2090/3966* (2016.02)

(58) Field of Classification Search
CPC .. A61M 27/00; A61M 27/002; A61M 27/008; A61B 17/3415; A61B 17/3417; A61B 2017/3456; A61N 2017/3456
See application file for complete search history.

(56) References Cited

U.S. PATENT DOCUMENTS

| | | | | |
|---|---|---|---|---|
| 4,432,752 A | * | 2/1984 | Marlon | A61M 25/06 |
| | | | | 604/500 |
| 4,684,369 A | | 8/1987 | Wildemeersch | |
| 4,976,684 A | | 12/1990 | Broadnax | |
| 5,336,177 A | | 8/1994 | Marcus | |
| 5,431,661 A | | 7/1995 | Koch | |
| 5,800,409 A | * | 9/1998 | Bruce | A61B 17/3421 |
| | | | | 604/523 |
| 2005/0027282 A1 | | 2/2005 | Schweikert et al. | |
| 2007/0078396 A1 | * | 4/2007 | Feeley | A61B 17/3415 |
| | | | | 604/164.01 |

(Continued)

OTHER PUBLICATIONS

PCT International Search Report and Written Opinion of the International Search Authority for corresponding publication No. WO2022/177882, dated Apr. 28, 2022.

*Primary Examiner* — Katherine M Rodjom

(74) *Attorney, Agent, or Firm* — Morgan, Lewis & Bockius LLP

(57) ABSTRACT

A surgical drain including an introducer having a central axis, a proximal end, and a distal end. The proximal end disposed along the central axis and configured to couple to a drain. The distal end having a blunt distal tip and the introducer at least partially tapering from the proximal end to the distal end, wherein the introducer has a length of 30 cm or greater.

19 Claims, 9 Drawing Sheets

(56)        References Cited

U.S. PATENT DOCUMENTS

| 2009/0204140 | A1* | 8/2009 | Dandl | ................. | A61B 17/3417 |
| | | | | | 606/185 |
| 2014/0296769 | A1* | 10/2014 | Hyde | .................. | A61M 27/002 |
| | | | | | 604/9 |
| 2017/0156800 | A1* | 6/2017 | Brown | ................. | A61B 6/4441 |
| 2020/0261114 | A1 | 8/2020 | Levine et al. | | |
| 2021/0001105 | A1* | 1/2021 | Schmidt | ............ | A61M 39/0247 |
| 2021/0154379 | A1* | 5/2021 | Tandon | ................. | A61M 1/962 |

* cited by examiner

SURGICAL DRAIN DEVICE AND METHOD OF USE

CROSS-REFERENCE TO RELATED APPLICATIONS

This application is a continuation of International Patent Application No. PCT/US22/16410 filed Feb. 15, 2022 which claims the benefit of U.S. Provisional Patent Application No. 63/150,222 filed Feb. 16, 2021 entitled "Surgical Drain Introducer and Method of Use", each of which is incorporated by reference herein in its entirety.

FIELD OF THE INVENTION

The present invention generally relates to surgical drains for use for removing fluids, such as liquids and gases, from a wound or during surgery and, more particularly, to an introducer used with a surgical drain for removing fluids from a wound or during surgical procedures and methods of using the same.

BRIEF SUMMARY OF THE DISCLOSURE

One embodiment of the present invention provides a surgical drain including an introducer having a central axis, a proximal end, and a distal end, the proximal end disposed along the central axis and configured to couple to a drain, and the distal end having a blunt distal tip, the introducer at least partially tapering from the proximal end to the distal end, wherein the introducer has a length of 30 cm or greater.

In some embodiments, the proximal end includes one or more ferrules extending radially from the central axis. The drain may be coupled to the introducer and the one or more ferrules may be friction fit with an inner surface of the drain to resist decoupling the drain from the introducer.

In some embodiments, the one or more ferrules are tapered and frustoconically shaped. The one or more ferrules may include a plurality of tapered ferrules forming a saw-tooth cross sectional profile.

In some embodiments, the surgical drain further includes a middle portion disposed between the proximal end and the distal end, the middle portion having an arc resulting in the distal end being offset from the central axis.

In some embodiments, the introducer is configured to curve in a radial direction along a portion of the introducer. The distal end may be offset from the central axis. The distal end may be offset from the central axis by approximately 30 degrees.

In some embodiments, a diameter of the proximal end is greater than a diameter of the distal end.

In some embodiments, the introducer is comprised of a rigid material. The introducer may include one or more gripping portions. The introducer may include at least one radiopaque marker.

In some embodiments, one or both of a portion of the middle portion and a portion of the distal curves away from the central axis.

In some embodiments, a maximum diameter of a portion adjacent the proximal end is greater than the diameter of the distal end. The introducer may have a maximum diameter of approximately 0.5 cm.

In some embodiments, the introducer constantly tapers from a portion proximate the proximal end toward a portion proximate the distal end.

In some embodiments, a ratio of the length of the introducer to a maximum diameter of the introducer is greater than 50:1. A ratio of the length of the introducer to a maximum diameter of the introducer may be greater than or equal to 80:1. A ratio of the length of the introducer to a maximum diameter of the introducer may be greater than or equal to 100:1. A ratio of the length of the introducer to a maximum diameter of the introducer may be greater than or equal to 120:1.

Another embodiment of the present invention provides a surgical drain including an introducer comprised of a rigid material having a central axis, a proximal end, a middle portion, and a distal end, the proximal end disposed along the central axis and configured to couple to a flexible drain and the distal end offset from the central axis and having a blunt distal tip, the introducer at least partially tapering from the proximal end to the distal end, wherein the introducer has a length greater than or equal to 30 cm, a maximum diameter of at least 0.5 cm, and curves in a radial direction along a portion of the introducer.

Another embodiment of the present invention provides a method of using a surgical drain including inserting a surgical drain through an entrance site to a first location disposed within a body of a patient, the entrance site being located on a skin of the patient, the surgical drain including an introducer having a central axis, a proximal end, and a distal end, the proximal end disposed along the central axis and configured to couple to a drain, and the distal end having a blunt distal tip, the introducer at least partially tapering from the proximal end to the distal end, threading the introducer of the surgical drain from the first location to a second location, the second location being disposed within the body of the patient, pressing the introducer against an exit site located adjacent the first location, the exit site being disposed on the skin of the patient, and making a distal incision at the exit site and moving the introducer through the distal incision.

In some embodiments, a drain coupled to the introducer provides fluid communication between a first area proximate the first location and a second area proximate the second location.

In some embodiments, the entrance site is disposed adjacent the first location and the entrance site is superficial to the first location.

In some embodiments, pressing the introducer against the exit site located results in the skin of the patient tenting outward in a superficial direction to indicate a location where the distal incision is to be made.

BRIEF DESCRIPTION OF THE DRAWINGS

The following detailed description of embodiments of the surgical drain device, will be better understood when read in conjunction with the appended drawings of an exemplary embodiment. It should be understood, however, that the invention is not limited to the precise arrangements and instrumentalities shown.

DETAILED DESCRIPTION

Draining of fluids from wounds or during surgery is important to prevent infection or other complications. Surgical drains comprising tubing may be used to provide a route for fluids to exit a target site located within a patient's body. For example, surgical drains may be used during minimally invasive surgeries, such as laparoscopic procedures, to drain fluid from within the body, such as the abdomen. Due to the flexible and malleable nature of surgical drains, rigid introducers may be coupled to the end of a surgical drains to thread the surgical drain from the target site to an exit point outside the patient's body.

Figure 1:
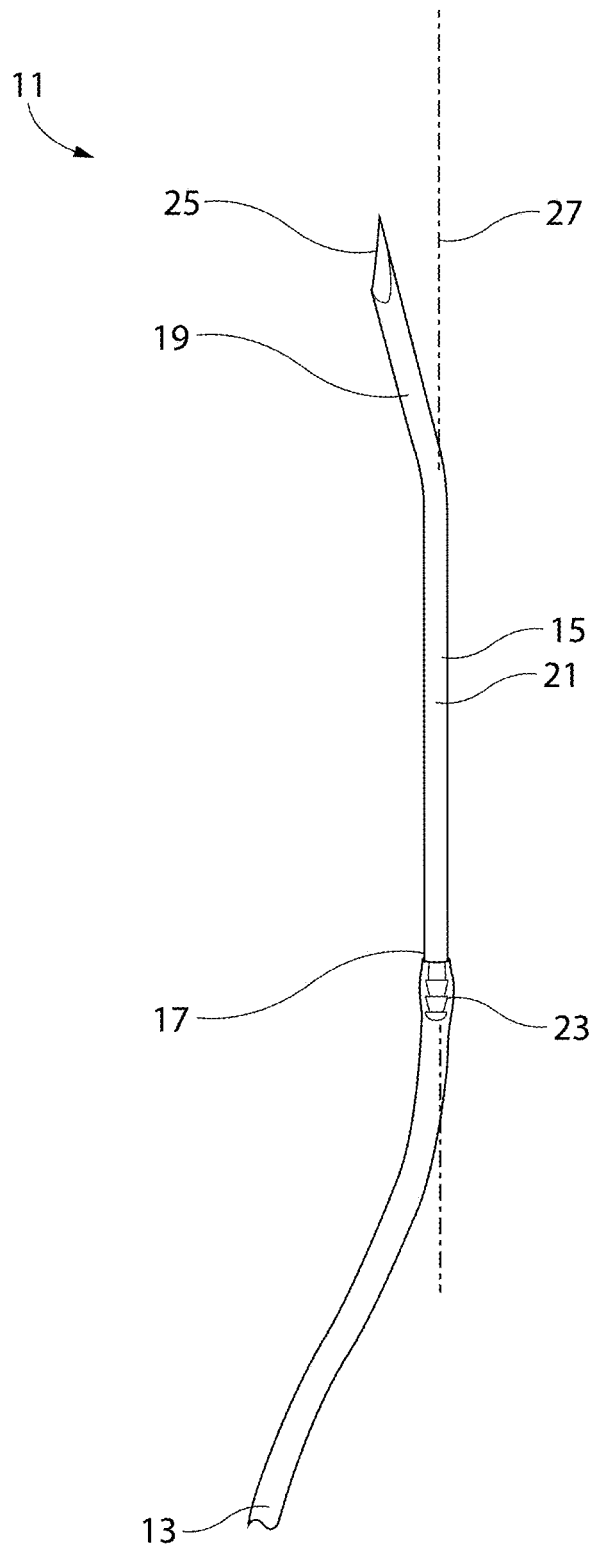
FIG. 1 is side view of a prior art surgical drain device.

Referring to FIG. 1, existing surgical drain devices include introducers that have been used to introduce and thread a surgical drain through various tissues of a patient. As shown in FIG. 1, a known surgical drain device 11 may be include drain 13 and may include introducer 15.

Introducer 15 may include proximal end 17, middle portion 21, distal end 19, distal tip 25, and central axis 27. Middle portion 21 may be disposed between proximal end 17 and distal end 19. Distal tip 25 may be located on an end of distal end 19. In some embodiments, introducer 15 is coupled to drain 13. Introducer 15 may be coupled to drain 13 via coupling element 23, which may be disposed adjacent proximal end 17. In some embodiments, distal tip 25 of introducer 15 is sharp and pointed to allow distal tip 25 to penetrate tissue. For example, distal tip 25 may be sharp and pointed to allow a user to insert introducer 15 into a patient's skin at a first location (e.g., entry point). Introducer 15 may then be threaded through the patient's tissue and may exit the patient's skin at a second location (e.g., exit point).

Current introducers, such as introducer 15, include one or more sharp distal ends that are configured to penetrate the skin of a patient. These sharp distal ends may cause damage to surrounding tissue as the introducer is threaded from the first location and/or the target site to the exit point. For example, distal tip 25 of introducer 15 may be sharp and pointed to allow introducer 15 to be inserted into a patient's skin, threaded through tissue of the patient, and then exit the patient's skin at an exit point. In use, introducer 15 may be inserted into a patient's skin adjacent their ribs or between their ribs and may exit the patient through the abdomen to thread and place surgical drain device 11 at a target site disposed within the patient's body, such as their chest cavity. This allows for the draining of fluid, such as liquids and gases, via drain 13 from the target site to outside the patient. However, during use of introducer 15, the sharp and pointed distal tip 25 may cause inadvertent perforation or damage of tissue when introducer 15 is being threaded and manipulated by the surgeon or user.

In some embodiments, middle portion 21 of introducer 15 includes a bend such that a portion of middle portion 21 and distal end 19 are offset relative to central axis 27. Further, current introducers, such as introducer 15, are too short to allow for manipulation by a surgeon. Introducer 15 may have a length of 15 cm to allow a user to thread introducer 15 through tissue, which may be too short to allow for manipulation by a surgeon or robot during robotic surgeries. For example, during limited incision surgeries or minimally invasive surgeries (e.g., laparoscopic or robotic surgeries), longer introducers may be preferred due to the minimal size and limited number of incisions/ports made in the patient during the limited incision surgery or minimally invasive surgery.

Referring to FIGS. 2-8, there is shown a surgical drain device, generally designated 100 or 100', in accordance with exemplary embodiments of the present invention. In use, surgical drain device 100, 100' may facilitate the delivery of a surgical drain to a target site within the body of a patient during limited incision surgeries, such as limited-incision facelifts or neck lifts, or minimally invasive surgeries, such as laparoscopic surgery or robotic surgery. The surgical drain may be substantially hollow throughout to provide a route for draining fluid that have accumulated at the target site inside the patient. Specifically, surgical drain device 100, 100' may allow for threading a surgical drain through a target site such that one end of the surgical drain remains at the target site and the other end is threaded to a location outside the patient's body to provide a route for fluid to exit from the target site inside the patient to an external location. For example, surgical drain device 100, 100' may be used to drain liquids from the body such as blood, serous fluid, serosanguineous fluid, seropurulent fluid, or purulent fluid, or gases from the body such as carbon dioxide, nitrous oxide, helium, or ambient air.

Figure 2:
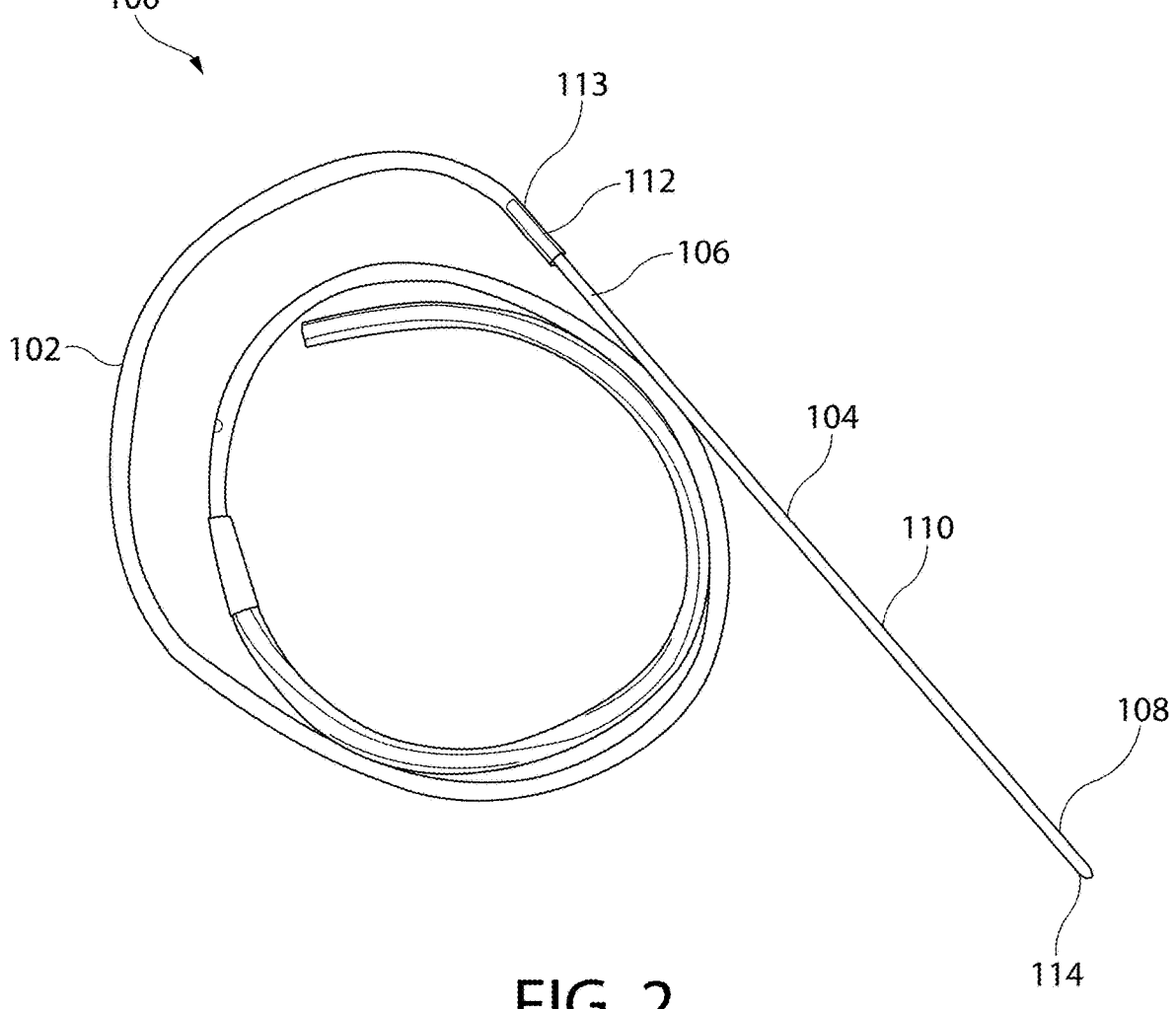
FIG. 2 is a side view of a surgical drain device in accordance with an exemplary embodiment of the present invention.
Figure 3:
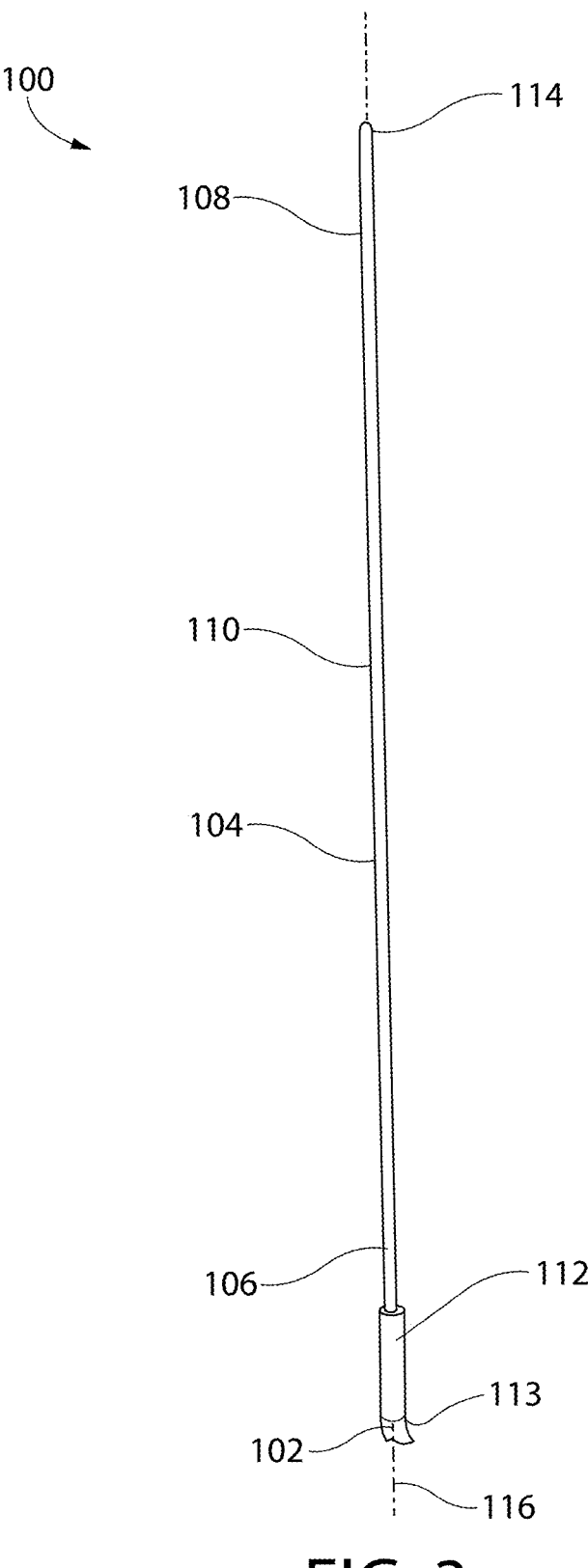
FIG. 3 is a zoomed in view of the surgical drain device of FIG. 2.

As shown in FIGS. 2-3, surgical drain device 100 may include trocar or introducer 104 and drain 102. Introducer 104 may be coupled to drain 102. Introducer 104 may include proximal end 106, middle portion 110, distal end 108, distal tip 114, and central axis 116. Middle portion 110 may be disposed between proximal end 106 and distal end 108. In some embodiments, distal tip 114 is disposed adjacent or proximate distal end 108. In some embodiments, central axis 116 is disposed along the entire length of introducer 104. For example, central axis 116 may extend through the entire length of introducer 104. In some embodiments, introducer 104 is substantially devoid of any bends or curves such that the entirety of introducer 104 extends along central axis 116. However, introducer 104 may include one or more curves or bends causing one or more portions of introducer 104 to deviate from central axis 116.

Referring to FIGS. 2-3, introducer 104 may be configured to couple to drain 102. In some embodiments, introducer 104 is coupled to drain 102 adjacent proximal end 106. In some embodiments, drain 102 may be removably coupled to introducer 104. In other embodiments, drain 102 may be fixedly coupled. Drain 102 may be coupled to introducer 104 via fasteners, clamps, barbs, ribs, adhesives, friction or press fitting, and/or any other attachment methods.

Introducer 104 may include one or more coupling elements 112 to securely couple drain 102 to introducer 104 to prevent drain 102 from inadvertently decoupling from introducer 104. In some embodiments, proximal end 106 of introducer 104 includes coupling element 112. Drain 102 may be coupled to introducer 104 (e.g., proximal end 106) via friction fitting coupling element 112 into drain 102 to allow drain 102 to be disposed around proximal end 106 to prevent drain 102 from inadvertently decoupling from introducer 104 during use. However, coupling element 112 may include an adhesive, epoxy, interlocking mechanism, or any other feature to couple drain 102 to introducer 104.

In some embodiments, drain 102 is coupled to coupling element 112, which may tether introducer 104 to drain 102. For example, coupling element 112 may be coupled to drain 102 at one end and introducer 104 at another end. Coupling element 112 may be removably coupled to drain 102 to allow introducer 104 and coupling element 112 to be removed from drain. In some embodiments, coupling element 112 is fixedly coupled to introducer 104. For example, coupling element 112 may be welded to introducer 104 such that coupling element 112 is fixedly coupled to introducer 104. However, coupling element 112 may be removably coupled to introducer 104. In some embodiments, coupling element 112 is removably coupled to drain 102 to allow drain 102 to be easily replaced. In some embodiments, coupling element 112 is configured to prevent leakage from drain 102 when introducer 104 is coupled to drain 102. For example, coupling element 112 may be configured to prevent leakage when fluids, gases, and/or objects flow from drain 102 to introducer 104.

In some embodiments, drain 102 includes proximal end 113 that may be the portion of drain 102 coupled to introducer 104. For example, introducer 104 and/or coupling element 112 may be inserted into proximal end 113 of drain 102 to couple introducer 104 to drain 102. In some embodiments, proximal end 106 of introducer 104 includes a tapered portion that is inserted into proximal end 113 of drain. Proximal end 106 including a tapered portion may assist in inserting introducer 104 into proximal end 113 of drain 102. In some embodiments, introducer 104 is press fitted into proximal end 113 of drain 102. Proximal end 113 of drain 102 may be coupled to proximal end 106 of introducer 104 via one or more coupling elements 112.

Figure 4:
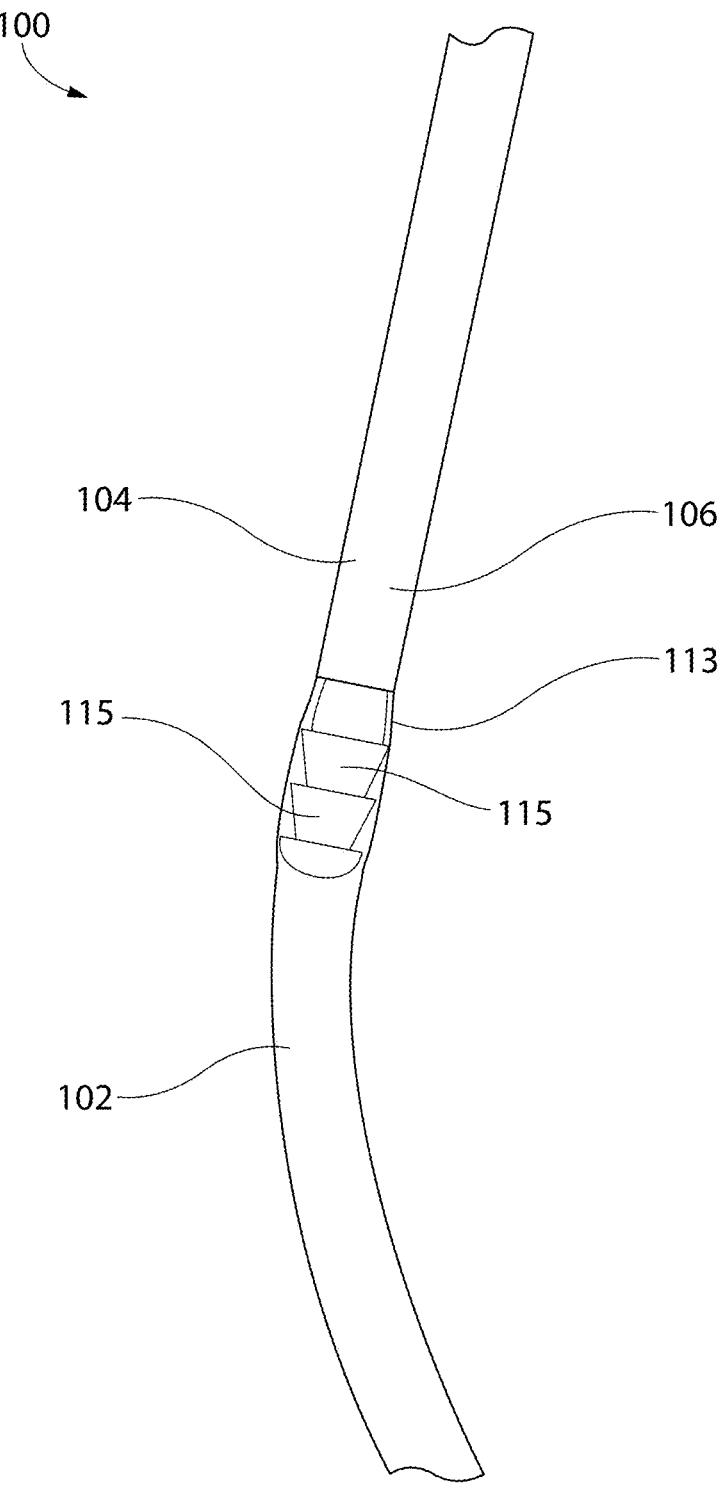
FIG. 4 is a side view of a portion of a surgical drain device having a plurality of ferrules in accordance with an exemplary embodiment of the present invention.
Figure 5:
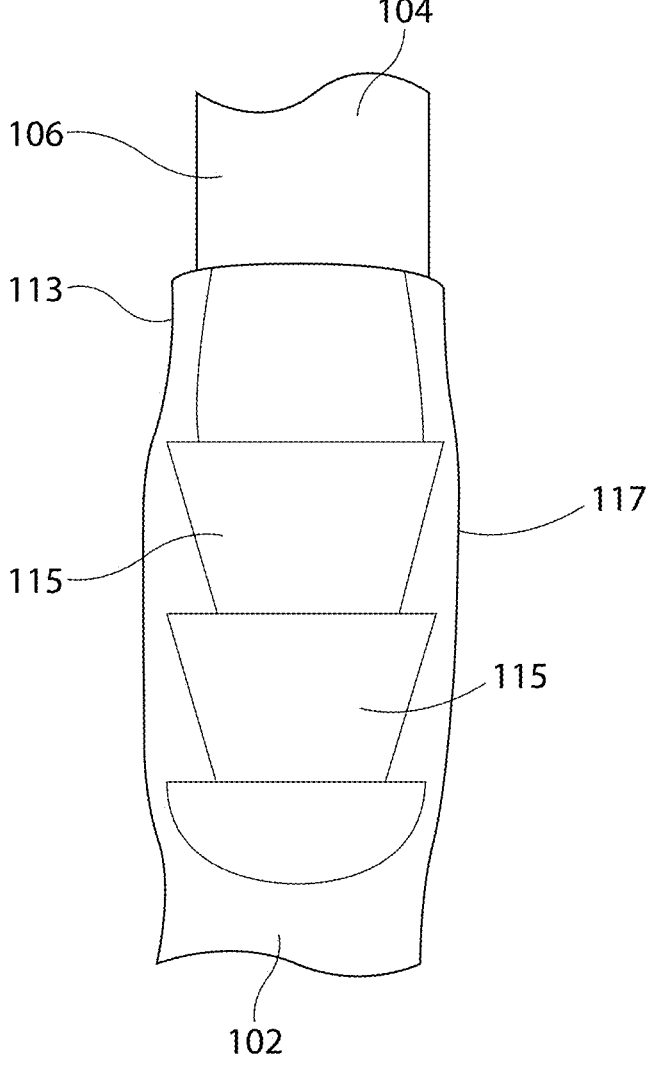
FIG. 5 is a zoomed in view of the surgical drain device of FIG. 4.

Referring to FIGS. 4-5, coupling element 112 may include one or more ferrules 115 to assist in coupling introducer 104 to drain 102. For example, coupling element 112 and/or proximal end 106 of introducer 104 may include one or more ferrules 115 to secure proximal end 113 of drain 102 to introducer 104. In some embodiments, ferrules 115 are tapered-shaped ferrules. For example, each ferrule 115 may be a tapered cylinder of material disposed proximate proximal end 106 of introducer 104. Ferrules 115 may include frustoconically shaped ribs or protrusions to form a saw-tooth cross-sectional profile. In some embodiments, a portion of each ferrule 115 proximate proximal end 106 has a greater diameter than a portion of ferrule 115 distal to proximal end 106. Ferrule 115 may be coupled to proximal end 106 of introducer 104, and introducer 104 and ferrule 115 may be inserted into proximal end 113 of drain 102, thereby coupling drain 102 to introducer 104. For example, one or more ferrules 115 may be fixedly coupled or removably coupled to introducer 104. In some embodiments, one or more ferrules 115 are integrally formed with introducer 104 such that one or more ferrules 115 and introducer 104 form a unitary structure. Ferrules 115 may be further coupled to introducer 104 via fasteners, welding, adhesives, and/or any other coupling method. In some embodiments, proximal end 106 includes one or more ferrules 115, which are configured to contact inner surface 117 of drain 102. One or more ferrules 115 contacting inner surface 117 of drain 102 may result in friction between ferrules 115 and inner surface 117 to prevent drain 102 from inadvertently detaching from proximal end 106 of introducer 104.

In some embodiments, ferrule 115 is tapered on the end distal proximal end 106 compared with the end proximate proximal end 106 to securely couple introducer 104 to drain 102. Ferrule 115 may be tapered on the end distal to proximal end 106 to allow introducer 104 and ferrule 115 to be easily inserted into end 113 of drain 102 but preventing inadvertent decoupling. In some embodiments, one or more ferrules 115 include barb-like protrusions angled to allow introducer 104 to be more easily inserted into drain 102 and more difficult to remove. For example, ferrule 115 may have one or more one-way barb-like protrusions to allow introducer 104 to be inserted into drain 102 and prevent, or at least resist, decoupling. In some embodiments, two or more ferrules 115 are stacked together proximate proximal end 106 of introducer 104. For example, introducer 104 may include two, three, four, five, six, seven, eight, nine, ten, or greater than ten ferrules 115 stacked together proximate proximal end 106. Two or more ferrules 115 may be stacked such that a portion of one ferrule 115 is inserted into a portion of an adjacent ferrule 115. For example, two or more ferrules 115 may be stacked together such that a narrower end of one ferrule 115 is inserted into a wider end of an adjacent ferrule 115. However, drain 102 may include one or more ferrules 115 having protrusions arranged in a saw-tooth configuration such the cross-section of one or more ferrules 115 resembles a saw-tooth pattern or wave. In some embodiments, a single ferrule 115 includes protrusions arranged in a saw-tooth configuration such that the cross-section of the single ferrule 115 resembles a saw-tooth pattern or wave. For example, a single ferrule 115 may be coupled to introducer 104 and the single ferrule 115 may have a plurality of frustoconically shaped ribs or protrusions arranged in a saw-tooth configuration. In some embodiments, ferrule 115 is comprised of metal. However, ferrule 115 may be comprised of plastic, a metallic alloy, stainless steel, PVC, or any other biocompatible material.

In some embodiments, drain 102 is coupled to introducer 104 by heating drain 102 such that it melts and/or conforms to proximal end 106 of introducer 104 and/or coupling element 112. In some embodiments, drain 102 is heated such that it melts and/or conforms around ferrules 115 disposed on introducer 104. However, introducer 104 may be heated and inserted into drain 102 such that drain 102 melts and/or conforms around proximal end 106 of introducer 104 and/or coupling element 112. In some embodiments, introducer 104 and/or ferrule 115 are heated and inserted into drain 102. In yet another embodiment, introducer 104 is inserted into drain 102 and both introducer 104 and drain 102 are heated such that drain 102 melts and/or conforms around proximal end 106 of introducer 104 or coupling element 112. In some embodiments, drain 102 may be further secured to introducer 104 via one or more ferrules 115 coupled to proximal end 106 of introducer 104. In some embodiments, coupling introducer 104 to drain 102 allows introducer 104 to be in fluid communication with drain 102. Ferrules 115 may be used to prevent leakage when fluids and/or objects flow from drain 102 to introducer 104.

In some embodiments, introducer 104 is comprised of a rigid metal. For example, introducer 104 may be comprised of metal. However, introducer 104 may be comprised of metal, a metallic alloy, stainless steel, plastic, PVC, silicon, or fluoropolymers. In some embodiments, introducer 104 is comprised of material more rigid than the material comprising drain 102. For example, drain 102 may be comprised of flexible plastic, whereas introducer 104 is comprised of a material more rigid than flexible plastic, such as stainless steel. In some embodiments, introducer 104 is comprised of a rigid material to prevent bending or breaking of introducer 104 when introducer 104 is being threaded through tissue of a patient. In some embodiments, introducer 104 is comprised of a biocompatible rigid material to allow introducer 104 to be threaded through tissues within a patient's body without causing irritation or infection of the tissue. In some embodiments, introducer 104 is comprised of a material that is configured to be sterilized. For example, introducer 104 may be comprised of an autoclavable material to allow introducer 104 to be sterilized and reused.

In some embodiments, introducer 104 may be configured to be bendable and/or moldable to a shape desired by the user. For example, one or more portions of introducer 104 may be configured to bend to the desired radius of curvature. Introducer 104 may include middle portion 110 disposed between proximal end 106 and distal end 108. Proximal end 106 may be located adjacent drain 102 and coupling element 112. Proximal end 106 may be disposed along central axis 116. Proximal end 106, middle portion 110, and distal end 108 may initially be disposed along central axis 116 and portions of introducer 104 may then be configured to bend and/or curve such that one or more of portions of proximal end 106, middle portion 110, and/or distal end 108 are offset from central axis 116. In some embodiments, introducer 104 may retain rigidity after being molded to the desired shape. For example, introducer 104 may be comprised of a material that is configured to be heated to allow introducer 104 to be molded to the desired shaped, and then cooled to maintain the desired shape in addition to being substantially rigid during normal use.

In some embodiments, introducer 104 is hollow. Introducer 104 being hollow may allow introducer 104 to be in fluid communication with drain 102. For example, introducer 104 may be hollow and fluid may be able to flow from drain 102 through introducer 104. In some embodiments, introducer 104 is configured to be any shape desired while still retaining the ability to transfer fluids and/or objects.

In some embodiments, distal tip 114 may be a blunt tip. For example, distal tip 114 may be blunt to prevent inadvertent perforation of or damage to tissue during use of surgical drain device 100. In some embodiments, distal tip 114 may include an interchangeable tip to allow for either a sharp tip or a blunt tip. For example, a user may couple the desired tip to distal tip 114, such as coupling either a sharp tip or blunt tip to distal tip 114. The user may switch the interchangeable tip to another desired tip. In some embodiments, distal tip 114 is blunt, but allows surgical drain device 100 to move and thread through the desired tissues from the target site to an exit point. The exit point may be a point located on the patient (e.g., on the patient's skin) where introducer 104 exits, thereby allowing drain 102 to exit. This forms a conduit between the target site, where the fluid has accumulated, and the exit point to allow the fluid to flow from the target site to the exit point, a point outside the patient's body. Distal tip 114 may be open or closed. For example, distal tip 114 may be open such that distal tip 114 is in fluid communication with the rest of introducer 104 and/or drain 102. Distal tip 114 being open allows fluids and/or objects to flow from drain 102, through introducer 104 and out of distal tip 114. However, distal tip 114 of introducer 104 may be closed to prevent flow out of distal tip 114.

In some embodiments, distal tip 114 being blunt prevents distal tip 114 from inadvertently piercing or penetrating the patient's skin and/or tissue, such as surrounding organs. In some embodiments, distal tip 114 being blunt allows the user to use introducer 104 to push the skin, from within the patient's body, in the superficial direction to cause the skin of the patient to tent outward. The pushing of the skin outward in the superficial direction causes tenting of the patient's skin which serves as a marker for the surgeon to make an incision thereby allowing introducer 104 to exit through the skin of the patient. In some embodiments, introducer 104 being tapered and distal tip 114 being blunt allows introducer 104 to be safely used during limited-incision surgeries or minimally invasive surgeries, such as robotic surgeries, laparoscopic surgeries, endoscopic surgeries, arthroscopic surgery, or vascular surgery. For example, introducer 104 being tapered and distal tip 114 being blunt prevents introducer 104 from penetrating blood vessels and causing internal bleeding, which is especially important during non-invasive surgeries.

Figure 6:
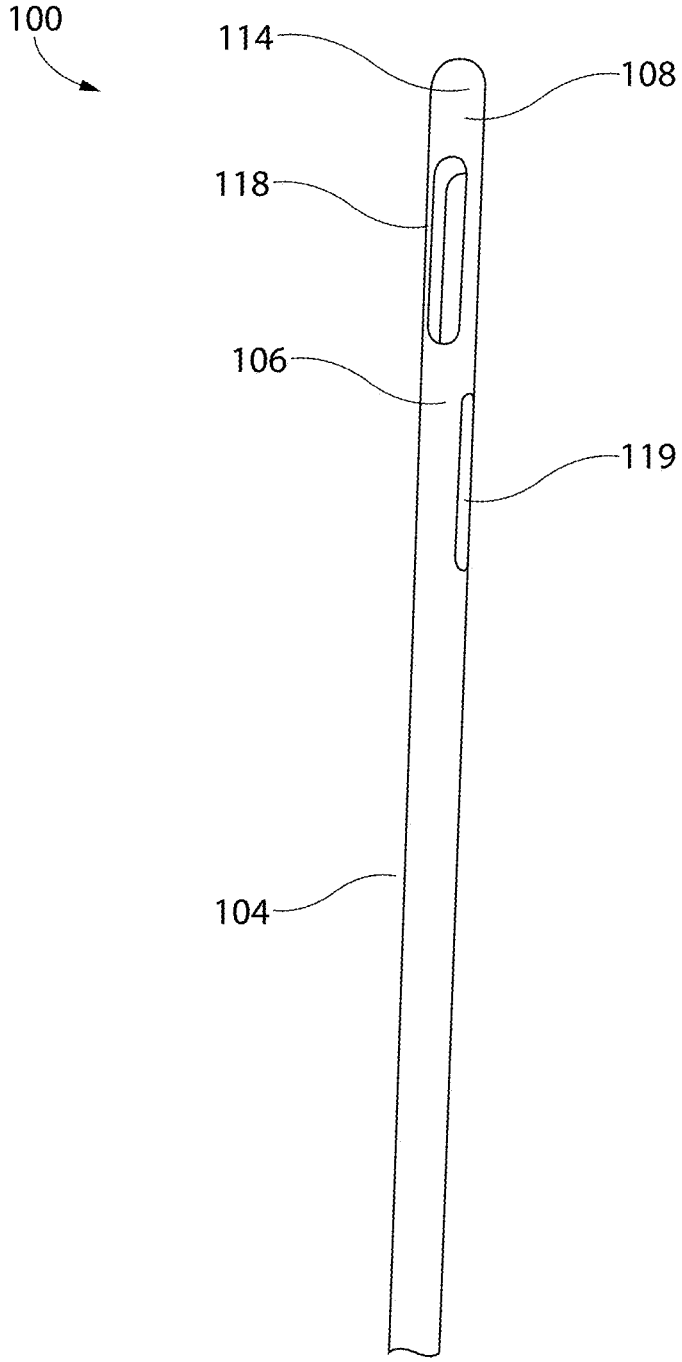
FIG. 6 is a side view of a portion of a surgical drain device having an aperture in accordance with an exemplary embodiment of the present invention.

Referring to FIGS. 3 and 6, introducer 104 may include one or more apertures 118. Aperture 118 may be disposed proximate distal end 108. In some embodiments, aperture 118 is disposed proximate distal tip 114. Since introducer 104 may be hollow, aperture 118 may allow fluids to flow from drain 102, through introducer 104, and out of distal tip 114. Aperture 118 may be sized and shaped to allow for fluids and/or objects to flow from drain 102 through introducer 104 and out of aperture 118. For example, aperture 118 may be circular, oval, elliptical, rectangular, or any other shape desired. In some embodiments, aperture 118 is elliptical in shape. For example, aperture 118 may have a length greater than its width. In some embodiments, aperture 118 extends in the distal to proximal direction along central axis 116 of introducer 104. Introducer 104 may include more than one aperture.

Figure 7:
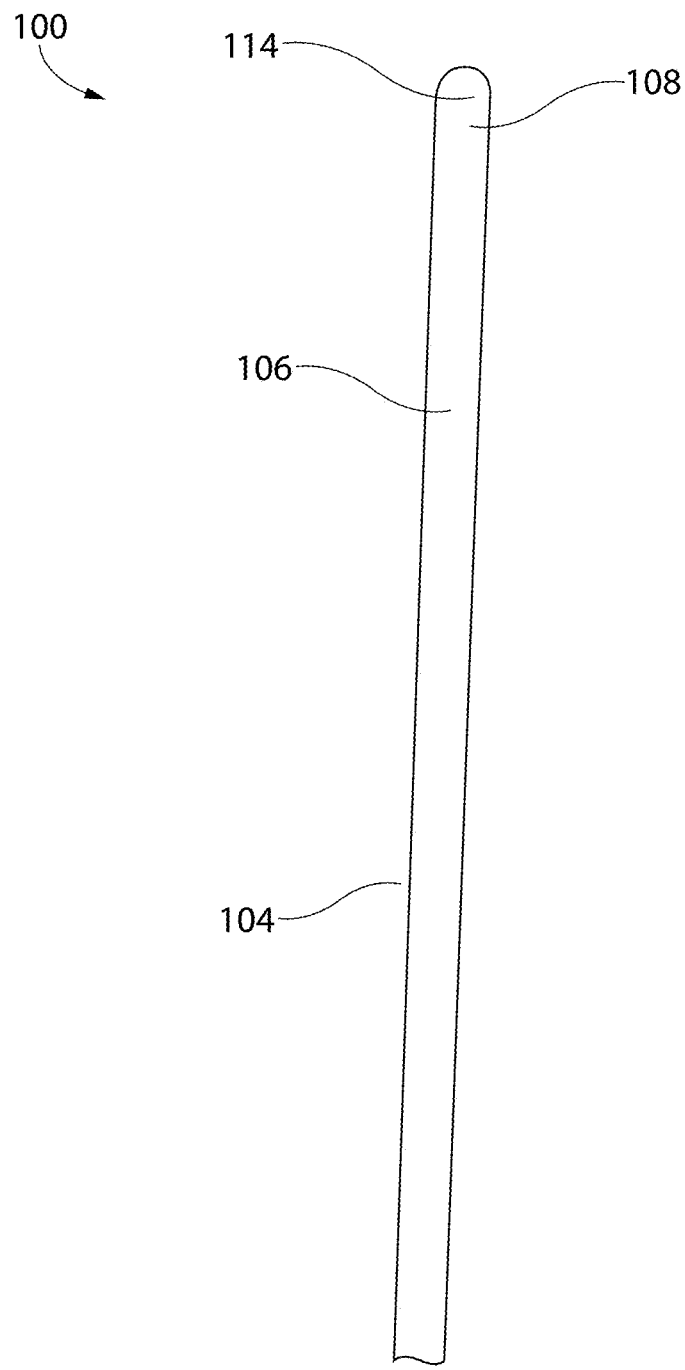
FIG. 7 is a side view of an embodiment of the surgical drain device of FIG. 6 without the aperture.

Referring to FIG. 7, introducer 104 may be devoid of any apertures along the length of introducer 104. For example, introducer 104 may not include any apertures between distal end 108 and proximal end 106.

In some embodiments, introducer 104 is coupled to an attachment, such as a suction system. For example, introducer 104 may be coupled to an attachment, such as a suction system, instead of drain 102, to allow fluids and/or objects to flow out of introducer 104 via aperture 118. However, introducer 104 may be coupled to both drain 102 and an attachment. For example, introducer 104 may be coupled to both drain 102 and a suction system such that the suction system causes fluids and/or gases to flow through drain 102 and/or introducer 104.

In some embodiments, introducer 104 has a length between 30 cm and 60 cm. For example, introducer 104 may have a length of approximately 30 cm, approximately 40 cm, approximately 50 cm, or approximately 60 cm. In some embodiments, introducer 104 has a length of approximately 30 cm to approximately 60 cm, approximately 35 cm to approximately 55 cm, or approximately 40 cm to approximately 50 cm. Introducer 104 may have a length greater than 30 cm. Introducer 104 may have a length greater than introducer 15 to allow for easier manual manipulation of introducer 104 by a surgeon or robot.

Figure 8:
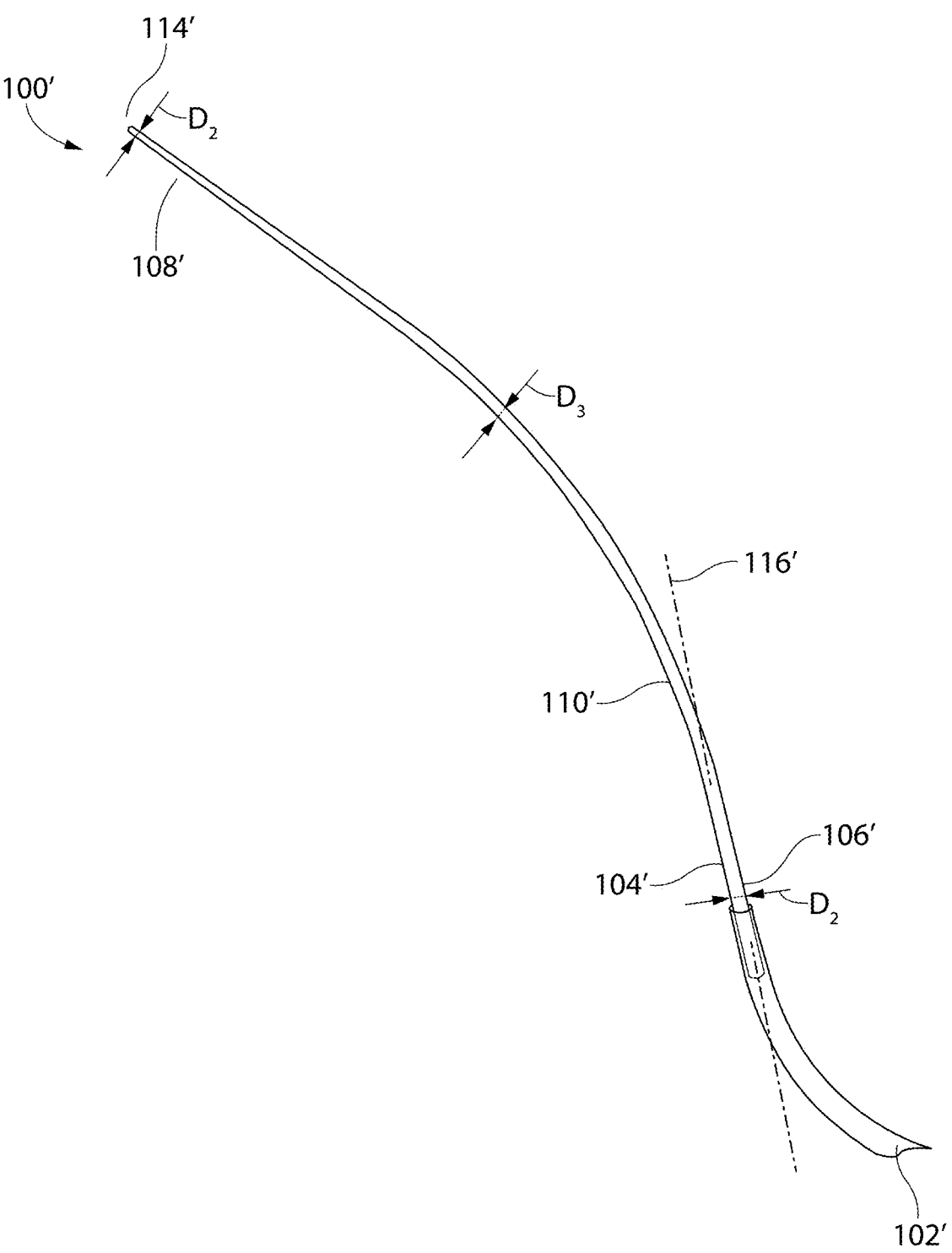
FIG. 8 is a side view of a surgical drain device having a curvature and a taper in accordance with a second exemplary embodiment of the present invention.

Referring to FIG. 8, there is shown a second exemplary embodiment. Surgical drain device 100' is similar to surgical drain device 100 shown in FIG. 2 and as discussed herein except that introducer 104' of surgical drain device 100' includes all of or a portion of middle portion 110' and distal end 108' being offset from central axis 116'. For example, all of or a portion of middle portion 110' may be offset from central axis 116' by between approximately 15° and approximately 45°. In some embodiments, all of or a portion of middle portion 110' and/or distal end 108' is offset from central axis 116' by approximately 15° to approximately 45°, approximately 20° to approximately 40°, or approximately 25° to approximately 35°. In a preferred embodiment, all of or a portion of middle portion 110 and/or distal end 108' is offset from central axis 116' by approximately 25° to approximately 30°. For example, middle portion 110' may be configured to curve away from central axis 116' resulting in middle portion 110' of introducer 104' forming an arc. In some embodiments, distal end 108' is configured to curve away from central axis 116' along with middle portion 110' resulting in distal tip 114' being offset from central axis 116'.

In some embodiments, distal end 108' is offset from central axis 116' more than middle portion 110'. However, middle portion 110' may be offset from central axis 116' more than or the same as distal end 108'. Introducer 104' may include one or more portions having an arc to allow for insertion through or adjacent a patient's ribcage, such as between the ribs, and exit via the abdomen. The curved nature of introducer 104' allows for introducer 104' to be threaded through tissue of the abdomen and retrieved at the exit point through the patient's skin. In some embodiments, introducer 104' is configured to curve in a radial direction along a portion of introducer 104'. Introducer 104' may be configured to curve in a first radial direction along a first portion of introducer 104' and along a second radial direction along a second portion of introducer 104'.

In some embodiments, introducer 104' includes a taper. Introducer 104' may taper along a portion of its length. In some embodiments, introducer 104' tapers at least for a portion between proximal end 106' to distal end 108'. For example, proximal end 106' may have diameter $D_1$ and distal end 108' may have diameter $D_2$, which is less than diameter $D_1$. Diameter $D_1$ may be approximately 0.5 cm and diameter $D_2$ may be approximately 0.25 cm. In some embodiments, diameter $D_1$ and diameter $D_2$ are between 0.1 cm and 2 cm. In some embodiments, introducer 104' tapers toward central axis 116'. Middle portion 110' may have diameter $D_3$, which may be less than or equal to diameter $D_1$ and greater than diameter $D_2$. For example, diameter $D_3$ may be 0.5 cm. In some embodiments, diameter $D_3$ is between 0.1 cm and 2 cm. In preferred embodiments, introducer 104' has a maximum diameter of approximately 0.5 cm.

In some embodiments, introducer 104' tapers from proximal end 106' to middle portion 110'. In other embodiments, introducer 104' tapers from proximal end 106' to distal end 108. In some other embodiments, introducer 104' tapers from middle portion 110' to distal end 108'.

Introducer 104' may continuously taper from one or more of proximal end 106' and middle portion 110' to distal end 108'. However, introducer 104' may have a greater taper from middle portion 110' to distal end 108' compared to the taper from proximal end 106' to middle portion 110'.

In some embodiments, introducer 104' may taper from middle portion 110' to distal end 108' and may be flat, with no taper, from proximal end 106' to middle portion 110'. In other embodiments, introducer 104' may taper from proximal end 106' to middle portion 110' and may be flat, with no taper, from middle portion 110' to distal end 108'. In some embodiments, introducer 104' may taper from diameter $D_3$ to diameter $D_2$. For example, introducer 104' may taper from 0.5 cm to 0.25 cm. In some embodiments, introducer 104' tapers over the last 3 cm of distal end 108. For example, introducer 104' may taper proximate distal tip 114'. In some embodiments, diameter $D_1$ is the maximum diameter of introducer 104'. For example, diameter $D_1$ may be the maximum diameter of introducer 104' and may be disposed adjacent proximal end 106', where drain 102' couples to introducer 104'. In some embodiments, introducer 104 includes a taper as mentioned herein.

Introducer 104' may have a ratio of length to maximum diameter of greater than 10:1. In some embodiments, introducer 104' has a ratio of length to maximum diameter of greater than 100:1. For example, introducer 104' may have a length of approximately 30 cm and a maximum diameter of approximately 2 cm resulting in a ratio of length to maximum diameter of 15:1. However, introducer 104' may have a ratio of length to maximum diameter of greater than or equal to 20:1, 25:1, 30:1, 50:1, 60:1, 75:1, 80:1, 100:1, 120:1, 150:1, or 200:1. In preferred embodiments, introducer 104' has a ratio of length to maximum diameter of greater than 50:1. In some embodiments, introducer 104 has a ratio of length to maximum diameter as mentioned herein.

In some embodiments, introducer 104 may include one or more gripping portions to allow a user to securely hold and manipulate introducer 104 without the concern for introducer 104 slipping. For example, introducer 104 may include one or more gripping portions disposed adjacent proximal end 106, middle portion 110, and/or distal end 108. Introducer 104 may include one or more gripping portions anywhere along introducer 104, such as between proximal end 106 and distal end 108. The gripping portions may include a plurality of ridges or protrusions or a material providing a frictional force between introducer 104 and the user's hand to prevent the user's hand from slipping off introducer 104 during manual manipulation of surgical drain device 100. In some embodiments, introducer 104' includes the one or more gripping portions mentioned herein.

In some embodiments, introducer 104 is hollow from proximal end 106 to distal end 108. For example, proximal end 106 may be in fluid communication with distal end 108 and introducer 104 may be configured to allow fluid from drain 102 to flow into proximal end 106 to distal end 108 and out of distal tip 114. In some embodiments, introducer 104' is hollow as mentioned herein.

Surgical drain device 100 may include one or more radiopaque markers. The one or more radiopaque markers may be disposed at various locations of surgical drain device 100. For example, introducer 104 and/or drain 102 may include one or more radiopaque markers. Surgical drain device 100 may include one, two, three, four, five, six, or any number of radiopaque markers desired. The radiopaque marker may be used with known imaging techniques and may be used to determine the location of surgical drain device 100 and may also aid in the retrieval or removal of surgical drain device 100 during complications that occur during surgery. In some embodiments, introducer 104' includes the one or more radiopaque markers mentioned herein.

Figure 9:
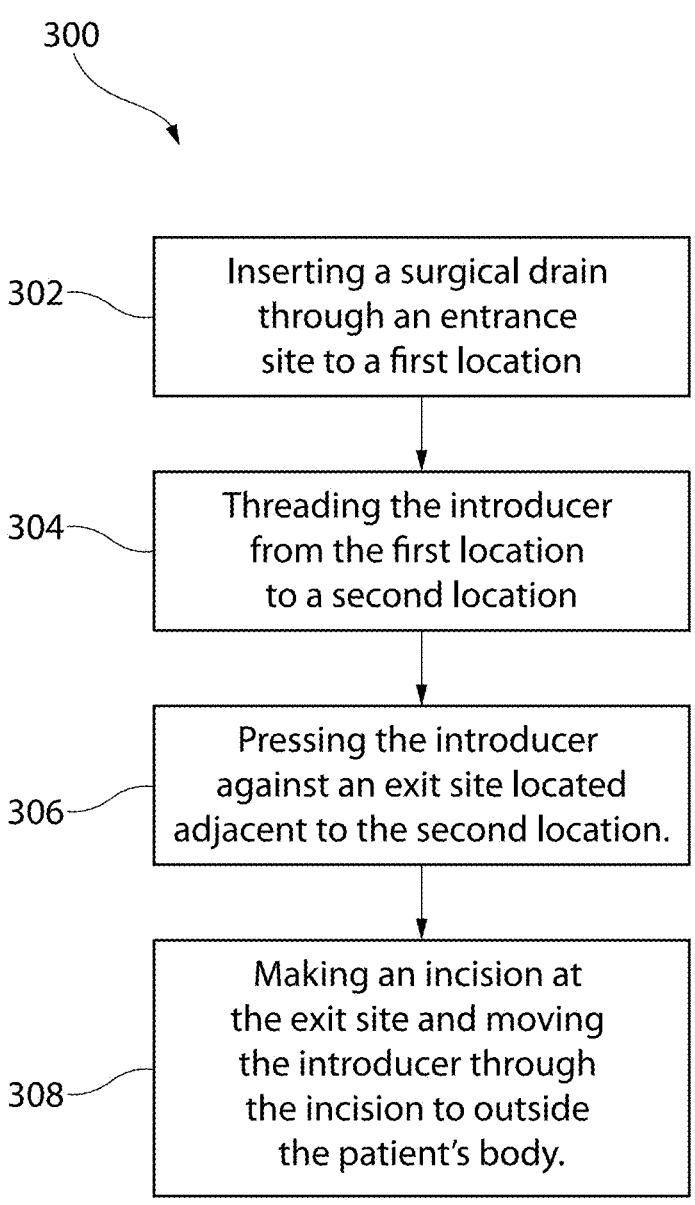
FIG. 9 is a flowchart showing an exemplary method of using the surgical drain devices of FIG. 2-8.

Referring to FIG. 9, exemplary method 300 of using surgical drain 100, 100' is shown. In some embodiments, introducer 104, 104' is coupled to drain 102, 102' and introducer 104, 104' is configured to be inserted into a patient's body to deliver drain 102, 102' to a first location, such as a target site, located within the patient's body. Introducer 104, 104' may enter the patient's body at an entrance site. For example, introducer 104, 104', coupled to drain 102, 102', may be inserted through the skin of a patient, at the entrance site, and threaded from a first location to second location. Introducer 104, 104' may exit through the patient's skin via an exit site located on the patient's skin, adjacent to the second location. Introducer 104, 104' may be pressed against the patient's skin from within the patient's body at the second location, resulting in the skin tenting outward (e.g., in the superficial direction) at the exit site. The skin tenting outward indicates the location of the exit site, where an incision needs to be made to allow introducer 104, 104' to exit the patient's body.

In some embodiments, introducer 104, 104' having blunt distal tip 114, 114' results in the skin of the patient tenting outward at the exit site when introducer 104, 104' is pressed up against the patient's skin from inside the patient. When the patient's skin is tented superficially outward at the exit site, an incision is made at that location and introducer 104, 104' is pulled out of the patient's body. In some embodiments, a portion of drain 102, 102' remains within the patient's body to allow the target site to be in fluid communication with a site outside the patient's body. For example, a portion of drain 102, 102' may remain at first location, second location, or any location between first location and second location to allow a conduit from the target site to a site or location outside the patient's body.

Method 300 may include step 302 of inserting surgical drain device 100, 100' through an entrance site to a first location disposed within the body of the patient. In some embodiments, the entrance site is located on the skin of the patient. Introducer 104, 104' may be inserted through an incision made at the entrance site and pushed to the first location. For example, an incision may be made on the skin of the patient adjacent the ribs and introducer 104, 104' may be placed within the incision and threaded to a first location disposed within the body adjacent the ribs. In some embodiments, Method 300 may include step 304 of threading introducer 104, 104' from the first location to a second location. In some embodiments, the second location is disposed within the body of the patient. For example, introducer 104, 104' may be threaded from the first location to the second location, such as the abdomen. In some embodiments, since introducer 104, 104' is coupled to drain 102, 102', threading introducer 104, 104' between locations also results in threading drain 102, 102' between locations. For example, threading introducer 104, 104' from the first location to the second location results in drain 102, 102' being disposed between the first location and the second location, thereby forming a fluid communication from an area proximate the first location to an area proximate the second location.

In some embodiments, method 300 includes step 306 of pressing introducer 104, 104' against an exit site located adjacent the second location. The exit site may be disposed on the skin of the patient. For example, once introducer 104, 104' is threaded from the first location to the second location, both which are disposed within the body of the patient, introducer 104, 104' is pressed against the skin from within the body at the exit site. In some embodiments, pressing introducer 104, 104' against the skin from within the body results in the skin tenting outward in the superficial direction at the exit site. The skin may tent in the superficial direction due to introducer 104, 104' having a blunt distal tip 114, 114'. In some embodiments, the skin tenting outward in the superficial direction indicates to the user where an incision needs to be made to allow introducer 104, 104' to exit the patient's body. Method 300 may include step 308 of making an incision at the exit site and moving the introducer through the incision at the exit site to outside the patient's body. It will be appreciated by those skilled in the art that changes could be made to the exemplary embodiments shown and described above without departing from the broad inventive concepts thereof. It is understood, therefore, that this invention is not limited to the exemplary embodiments shown and described, but it is intended to cover modifications within the spirit and scope of the present invention as defined by the claims. For example, specific features of the exemplary embodiments may or may not be part of the claimed invention and various features of the disclosed embodiments may be combined. The words "proximal", "distal", "upper" and "lower" designate directions in the drawings to which reference is made. Unless specifically set forth herein, the terms "a", "an" and "the" are not limited to one element but instead should be read as meaning "at least one".

It is to be understood that at least some of the figures and descriptions of the invention have been simplified to focus on elements that are relevant for a clear understanding of the invention, while eliminating, for purposes of clarity, other elements that those of ordinary skill in the art will appreciate may also comprise a portion of the invention. However, because such elements are well known in the art, and because they do not necessarily facilitate a better understanding of the invention, a description of such elements is not provided herein.

Further, to the extent that the methods of the present invention do not rely on the particular order of steps set forth herein, the particular order of the steps should not be construed as limitation on the claims. Any claims directed to the methods of the present invention should not be limited to the performance of their steps in the order written, and one skilled in the art can readily appreciate that the steps may be varied and still remain within the spirit and scope of the present invention.

What is claimed is:

1. A surgical drain introducer comprising:
   a central axis, a proximal end, and a distal end, the proximal end disposed along the central axis and opposite the distal end, the proximal end configured to couple to a drain, and the distal end having a blunt distal tip, the introducer constantly tapering from an area proximate the proximal end to an area proximate the distal end such that a diameter of the introducer decreases continuously along a length of the introducer from the proximal end to the distal end; and
   a middle portion disposed between the proximal end and the distal end and including the mid-point of the surgical drain introducer equidistance from the proximal end and distal end, the middle portion having an arc extending through the mid-point resulting in the distal end being offset from the central axis,
   wherein the introducer has a length of 30 cm or greater and the introducer is comprised of a rigid material to prevent bending of the introducer,
   wherein the introducer includes one or more apertures disposed proximate the distal end, the one or more apertures extending axially in the proximal direction along the central axis.

2. The surgical drain introducer according to claim 1, wherein the proximal end includes one or more ferrules extending radially from the central axis.

3. A surgical drain assembly comprising:
   the surgical drain introducer of claim 2; and
   the drain coupled to the introducer,
   wherein the one or more ferrules are friction fit with an inner surface of the drain to resist decoupling the drain from the introducer.

4. The surgical drain introducer according to claim 2, wherein the one or more ferrules are tapered and frustoconically shaped.

5. The surgical drain introducer according to claim 2, wherein the one or more ferrules include a plurality of tapered ferrules forming a saw-tooth cross sectional profile.

6. The surgical drain introducer according to claim 1 further comprising:
   a distal portion being straight; and
   a proximal portion being straight and shorter than the distal portion,
   wherein the arc of the middle portion extends from the proximal portion to the distal portion, and wherein the middle portion is longer than each of the proximal portion and the distal portion and extends more towards the proximal end than the distal end.

7. The surgical drain introducer according to claim 1, wherein the distal end is offset from the central axis by approximately 30 degrees.

8. The surgical drain introducer according to claim 1, wherein a diameter of the proximal end is greater than a diameter of the distal end.

9. The surgical drain introducer according to claim 1, wherein the introducer is comprised of stainless steel.

10. The surgical drain introducer according to claim 1, wherein the introducer includes one or more gripping portions disposed between the proximal end and the distal end, the one or more gripping portion including a plurality of ridges.

11. The surgical drain introducer according to claim 1, wherein the introducer includes at least one radiopaque marker.

12. The surgical drain introducer according to claim 1, wherein one or both of a portion of the middle portion and a portion of the distal end curves away from the central axis.

13. The surgical drain introducer according to claim 1, wherein a maximum diameter of a portion adjacent the proximal end is greater than the diameter of the distal end.

14. The surgical drain introducer according to claim 1, wherein the introducer has a maximum diameter of approximately 0.5 cm.

15. The surgical drain introducer according to claim 1, wherein a ratio of the length of the introducer to a maximum diameter of the introducer is greater than 50:1.

16. The surgical drain introducer according to claim 1, wherein a ratio of the length of the introducer to a maximum diameter of the introducer is greater than or equal to 80:1.

17. The surgical drain introducer according to claim 1, wherein a ratio of the length of the introducer to a maximum diameter of the introducer is greater than or equal to 100:1.

18. The surgical drain introducer according to claim 1, wherein a ratio of the length of the introducer to a maximum diameter of the introducer is greater than or equal to 120:1.

19. A surgical drain introducer comprising:

a central axis, a proximal end, a middle portion, and a distal end, the proximal end disposed along the central axis and opposite the distal end, the proximal end configured to couple to a flexible drain and the distal end offset from the central axis and having a blunt distal tip, the introducer constantly tapering from the proximal end to the distal end such that a diameter of the introducer continuously tapers and decreases along a length of the introducer from the proximal end, through the middle portion, and to the distal end;

a middle portion disposed between the proximal end and the distal end and including the mid-point of the surgical drain introducer equidistance from the proximal end and distal end, the middle portion having an arc extending through the mid-point resulting in the distal end being offset from the central axis;

one or more apertures disposed proximate the distal end, the one or more apertures extending axially in the proximal direction along the central axis and being radially and axially offset from one another;

one or more gripping portions disposed between the proximal end and the distal end, the one or more gripping portion including a plurality of ridges; and the flexible drain coupled to the introducer, wherein one or more ferrules disposed on the proximal end and extending radially from the central axis are friction fit with an inner surface of the drain to resist decoupling the drain from the introducer, wherein the introducer has a length greater than or equal to 30 cm, a maximum diameter of at least 0.5 cm, and curves in a radial direction along a portion of the introducer, and wherein the introducer is comprised of a rigid material to prevent bending of the introducer and the introducer includes a maximum diameter disposed adjacent the proximal end, wherein one or both of a portion of the middle portion and a portion of the distal end curves away from the central axis.

* * * * *